(12) United States Patent
Han et al.

(10) Patent No.: US 8,852,624 B2
(45) Date of Patent: Oct. 7, 2014

(54) BIOMEDICAL IMPLANTS COMPRISING SURFACE-MODIFIED CERAMIC PARTICLES AND BIODEGRADABLE STEREO COMPLEX POLYMERS, ITS USE FOR SUPPRESSING INFLAMMATION AND IMPROVEMENT OF MECHANICAL PROPERTY, AND PREPARATION METHOD THEREOF

(71) Applicant: Korea Institute of Science and Technology, Seoul (KR)

(72) Inventors: Dong Keun Han, Seoul (KR); Yoon Ki Joung, Seoul (KR); Jong Hee Kang, Seoul (KR); Ji Yeon Choi, Seoul (KR); Chang Hun Kum, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/633,342

(22) Filed: Oct. 2, 2012

(65) Prior Publication Data
US 2013/0280335 A1 Oct. 24, 2013

(30) Foreign Application Priority Data
Apr. 18, 2012 (KR) .................. 10-2012-0040480

(51) Int. Cl.
*A61K 9/50* (2006.01)
*A61K 31/74* (2006.01)

(52) U.S. Cl.
USPC ........... 424/423; 424/497; 424/490; 424/400; 977/773

(58) Field of Classification Search
USPC .................. 424/423, 490, 497, 400; 977/773
See application file for complete search history.

(56) References Cited

U.S. PATENT DOCUMENTS

| 2008/0014240 A1* | 1/2008 | Gale et al. ..................... 424/422 |
| 2008/0119927 A1* | 5/2008 | Lessar .......................... 623/1.42 |
| 2009/0240325 A1* | 9/2009 | Hsu et al. ..................... 623/1.46 |
| 2009/0297581 A1* | 12/2009 | Atanasoska et al. .......... 424/423 |

FOREIGN PATENT DOCUMENTS

KR 10-2012-0029130 3/2012

OTHER PUBLICATIONS

Chang Hun Kum et al., "2011 The Polymer Society of Korea Annual Meeting (Preparation of modified magnesium oxide and their enhancement of mechanical properties by stereocomplex structure)", Polymer Science and Technology vol. 22, No. 4, Oct. 6, 2011, pp. 1-4.
Korean Office Action mailed Jul. 24, 2013 in corresponding Korean Application No. 10-2012-0040480.
Koji Nagahama et al., "Biodegradable Stereocomplex Materials of Polylactide-grafted Dextran Exhibiting Soft and Tough Properties in Dry and Wet States", Journal of Polymer Science Part A: Polymer Chemistry 2012, vol. 50, pp. 2669-2676.

* cited by examiner

*Primary Examiner* — Frederick Krass
*Assistant Examiner* — Tracy Liu
(74) *Attorney, Agent, or Firm* — Staas & Halsey LLP

(57) ABSTRACT

A biomedical implant according to this invention comprises ceramic complex, which includes a surface-modified basic ceramic particles, which are basic ceramic particles modified their surface with first biodegradable polymers, and the second biodegradable polymers. The first and second biodegradable polymer are combined each other and form a stereo complex. The biomedical implant has a superior effect to suppress inflammation caused by degradation of biodegradable polymers with improving its mechanical property.

6 Claims, No Drawings

BIOMEDICAL IMPLANTS COMPRISING SURFACE-MODIFIED CERAMIC PARTICLES AND BIODEGRADABLE STEREO COMPLEX POLYMERS, ITS USE FOR SUPPRESSING INFLAMMATION AND IMPROVEMENT OF MECHANICAL PROPERTY, AND PREPARATION METHOD THEREOF

CROSS-REFERENCE TO RELATED APPLICATION

The present disclosure relates to subject matter contained in priority Korean Application No. 10-2012-0040480, filed on Apr. 18, 2012, which is herein expressly incorporated by reference in its entirety.

BACKGROUND OF THE INVENTION

1. Field of the Invention

The present disclosure relates to biomedical implants comprising surface-modified ceramic particles and biodegradable stereo complex polymers, its use for suppressing inflammation and improvement of mechanical property, and preparation method thereof.

2. Background of the Invention

Recently, due to development of the medical technology, biomedical implants acting as artificial organs or implantation materials have been used to substitute or recover damaged organs within human body. Applications of the biomedical implants have been gradually broadened, and thus, the researches into development of biomedical implants have been widely conducted. Materials used for preparing the biomedical implants include polymers, metals, ceramics, and composite materials. However, the material to be used in vivo must have biocompatibility with the host, and needs to have blood compatibility when exposed to blood, and needs to have tissue compatibility when exposed to biological tissues or cells, which places a limitation on available biomedical materials that can be utilized.

Thus, polymer materials having excellent formability and stable physical properties as well as being harmless to human body have been highlighted. In particular, because biodegradable polymers can minimize foreign body reaction caused by an immunological reaction developed when the biomedical implants are applied in vivo, due to their characteristics that they are degraded after a certain period of time.

However, biodegradable polymers have certain demerits, such as their physical properties being relatively poor compared with other polymers, and that when they are biodegraded, acidic materials such as lactic acid, glycolic acid, hydroxy caproic acid, maleic acid, phosphagen, hydroxy butyrate, hydroxyethoxy acetic acid, sebacic acid, alcohols, trimethylene glycol, amino acids, formalin, and alkylcyanoacrylate are generated, which cause inflammation reactions and cytotoxicity within human body.

Despite the shortcomings as mentioned above, biodegradable polymers have been widely used for biomedical implants owing to their characteristics of complete degradation after the lapse of a certain period of time. In addition, some methods to address to alleviate inflammation reactions resulting from biodegradable polymers usage have also been a suggested below.

For example, researches for finding an inflammation suppressing effect and improving physical properties by making biodegradable polymers used as implants have led to the use of contain non-steroidal anti-inflammatory drugs in ester series, such as salicylic acid and acetylsalicylic acid, had been conducted (J. Mater. Sci. Mater. Med., 13, pp. 1051-1055, 2002) and use of a method for suppressing both inflammation and restenosis by coating pyridoxal-5-phosphate on a stent has been suggested (WO 2006/056038).

In addition, a method for suppressing cell inflammation by making COX-2 protein and iNOS protein expressed with taheebo extract was suggested (KR 10-2008-0092263A) and a method to induce suppression of nitric oxide generation, as a byproduct of an inflammatory reaction, with gold and silver nano-particles have also been studied (KR 10-2009-0080855A).

However, one concern in regard to the above mentioned methods to suppress the already induced inflammations, which by contain an anti-inflammatory drug in biomaterials, in the risk of side effects due to the use of drugs.

Furthermore, any method to suppress the fundamental generation of acidic byproducts resulting from the degradation of biodegradable polymers has not yet been suggested. Namely, cellular inflammation, due to low pH of the acidic byproducts, have been constantly induced by the biodegradation of biodegradable polymers, but no fundamental solution thereto has been suggested, and there is a limitation on improvement of physical and mechanical properties of the biodegradable polymers.

SUMMARY OF THE INVENTION

An object of the present invention is to provide a method to suppress inflammation reaction and cytotoxicity caused by acidic byproducts, which is developed in using a biomedical implant, by making the acidic byproduct neutralized as to be harmless to human body and biodegradable basic ceramics.

Another object of the present invention is to provide a method to improve mechanical properties of biodegradable polymer materials, by increasing miscibility between basic ceramic particles and biodegradable polymers and forming stereo complex structure between the surface-modified basic ceramic particles and biodegradable polymers as well as controlling their basic features by modifying the surface of basic ceramic particles.

In order to achieve the objects, a biomedical implant according to an example of the present invention comprises ceramic complex. The ceramic complex comprises surface-modified basic ceramic particles which are basic ceramic particles modified their surface with the first biodegradable polymers and including the second biodegradable polymers, which combine with the above first biodegradable polymers to form a stereo complex. The basic ceramic particles may be neutralized acidic byproducts generated from degradation of polymers. The polymers may be selected from a group comprising the first biodegradable polymer, the second biodegradable polymer, or a combination thereof.

A method to prepare ceramic complex according to another example of the present invention comprises the following steps: (1) obtaining surface-modified basic ceramic particles by modifying the basic ceramic particles with first biodegradable polymers; and (2) mixing the surface-modified basic ceramic particles and second biodegradable polymers to be combined and to form stereo complex with the first biodegradable polymers included in the surface-modified basic ceramic particles.

A method to prepare a biomedical implant according to another example of the present invention comprises a process of preparing a biomedical implant, which includes a ceramic complex according to the above method.

The above biomedical implant may prevent interfacial delamination between the basic ceramic particles and polymers, which are the first or second biodegradable polymers, and improve the mechanical property thereof.

DETAILED DESCRIPTION OF THE INVENTION

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

A biomedical implant comprises ceramic complex. The ceramic complex comprises surface-modified basic ceramic particles which are basic ceramic particles modified their surface with first biodegradable polymers; and second biodegradable polymers. The second biodegradable polymers are combined with the first biodegradable polymers which are on the surface of the basic ceramic particles and then form a stereo complex.

The basic ceramic particles may be biocompatible ones. Also, the basic ceramic particles can neutralize acidic byproducts generated from degradation of the first or second biodegradable polymers. The basic ceramic particles can suppress fundamental generation of acidic byproducts during degradation of biodegradable polymers, and thus inflammation resulting therefrom can be suppressed.

In addition, the basic ceramic particles also have excellent compatibility with the biodegradable polymers, which is not seen in metal particles. The basic ceramic particles have functional groups on their surface, and they can chemically combine with the biodegradable polymers, and thus interfacial delamination between them can be prevented. Furthermore, it is possible to prevent phase separation both between the first biodegradable polymers and the basic ceramic particles and between the first biodegradable polymers and the surface-modified basic ceramic particles with improving mechanical strength of the ceramic complex greatly.

The ceramic particles may include ceramic compounds. The ceramic compound may be one of hydrated ceramic particles selected from the group comprising hydrated lithium oxide, hydrated beryllium oxide, hydrated sodium oxide, hydrated magnesium oxide, hydrated potassium oxide, hydrated calcium oxide, hydrated rubidium oxide, hydrated, strontium oxide, hydrated barium oxide, hydrated cesium oxide, hydrated francium oxide, hydrated radium oxide and their combinations. The ceramic compound may be one selected from the group comprising magnesium oxide, sodium oxide, lithium oxide, manganese oxide, potassium oxide, calcium oxide, barium oxide, cesium oxide, radium oxide and their combinations. The ceramic particles are basic, which can neutralize the acidic byproducts resulting from degradation of the first or second biodegradable polymers for suppressing inflammation caused by the acidic byproducts.

The ceramic particles may further include a metal selected from the group comprising alkali metal, alkaline earth metal and a combination thereof. Also, the ceramic particles may further include a metal compound selected from the group comprising alkali metal hydrate, alkaline earth metal hydrate, and a combination thereof. The alkali metals or the alkaline earth metals may be lithium, beryllium, sodium, magnesium, potassium, calcium, rubidium, strontium, barium, cesium, francium, or radium.

Surface area of the ceramic particles may change depending on their diameters, which results in change of the degree and speed of neutralization of the ceramic particles. The ceramic particles may have a diameter in the range of 1 nm to 1 mm. When the above ceramic particles have a diameter over 1 nm, surface modification of the particles can be accomplished properly and when the to diameter exceeds 1 mm, a polymer matrix including the first or second biodegradable polymers formed on the surface of the basic ceramic particles may crack and thus their physical property may be reduced.

The first biodegradable polymers used for surface modification of the basic ceramic particles may include one selected from the group comprising poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, polyglycolide-co-caprolactone, polydioxanone, polytrimethylene-carbonate, polyglycolide-co-dioxanone, polyamide ester, polypeptide, polyortho-esters, polymaleic acid, polyphosphazene, polyanhydride, polycebacicanhydride, polyhydroxyalkanoate, polyhydroxy butylate, polycyanoacrylate, and a combination thereof.

The second biodegradable polymers pairing with the above first biodegradable polymers for forming stereo complex may include one selected from the group comprising poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, polyglycolide-co-caprolactone, polydioxanone, polytrimethylene-carbonate, polyglycolide-co-dioxanone, polyamide ester, polypeptide, polyortho-esters, polymaleic acid, polyphosphazene, polyanhydride, polycebacicanhydride, polyhydroxyalkanoate, polyhydroxy butylate, polycyanoacrylate, and a combination thereof. When the stereo complex is formed with the second biodegradable polymers and the first biodegradable polymers on the surface modified basic ceramic particles, mechanical property of the biomedical implant can be improved.

The surface-modified basic ceramic particles may include 1 to 99 weight % (wt %) of the basic ceramic particles and 1 to 99 wt % of the first biodegradable polymers. The ceramic complex may include 1 to 99 wt % of the surface-modified basic ceramic particles and 1 to 99 wt % of the second biodegradable polymer.

It is desirable that content of the polymers containing the first biodegradable polymers and the second biodegradable polymers is 5 to 95 wt % and content of the basic ceramic particles is 5 to 95 wt % with respect to total weight of the ceramic complex. In the ceramic complex, according to a ratio by weight of the basic ceramic particles and the first and second biodegradable polymer, a speed and an amount of supplying materials for neutralizing the byproduct from the polymers can be controlled. Thus, when the content of the basic ceramic particles is less than 5 wt %, the content of the first and second polymers on the surface of ceramic particles may be too large to make the neutralization function from the basic ceramic particles. When the content of the ceramic particles exceeds 95 wt %, the surface modification by the polymer may not be sufficient.

The ceramic complex may be included in a coating layer on a biomedical implant, may comprise a biomedical implant, and may consist of a biomedical implant itself.

When a coating layer including the ceramic complex is formed on a conventional implant, the coating layer may contain the surface-modified basic ceramic particles of an amount of 1 wt % to 99 wt % and the second biodegradable polymer of an amount of 1 wt % to 99 wt %, with respect to total weight of the coating layer. As the degree of neutralization depends on the content of basic ceramic particles in the coating layer, it is possible to apply the coating to extensive biomedical implants by adjusting content ratio of the basic ceramic particles with the polymers.

When the biomedical implant is composed of the ceramic complex, content of the basic ceramic particles may be in the range of 1 wt % to 99 wt % and content of the first and second biodegradable polymers may be in the range of 1 wt % to 99 wt %. In the present invention, the content of the ceramic particles and the biodegradable polymers may be adjusted in the ranges above, by which the physical properties and the neutralization degree of biomedical implant can be controlled.

The biomedical implant may be one selected from the group comprising, but not limited to, cardiovascular system materials, such as a stent, surgical suture, scaffold for tissue regeneration, bio nano-fiber, hydrogel and bio-sponge; dental materials such as a pin, screw and bar; surgical materials including neurosurgery, orthopedic surgery, and plastic surgery; filler for plastic surgery, and bio-materials such as biosensor, biochip, and drug delivery system reservoir.

Any of the conventional biomedical implant may be composed of metal, ceramic, composite materials, non-degradable polymers, or biodegradable polymers. Materials of the conventional biomedical implant may be a metal selected from the group comprising iron, copper, gold, silver, platinum, stainless steel, cobalt-chromium, platinum-chromium, cobalt alloy, titanium, titanium alloy, tantalum, nickel-titanium, nickel, nickel alloy, magnesium, and magnesium alloy; a ceramic selected from the group comprising hydroxyapatite, TeCP, DCP, $NaH_2PO_4$, α-TCP, glycerophosphate, PHA, brushite, β-TCP, MCPM, $MgHPO_4$, $Na_4P_2O_7$ and $CaSO_4$; non-degradable polymers selected from the group to comprising acrylic resins such as polyethylene, polypropylene, polyvinylalcohol, polyvinylchloride, polystyrene, polycarbonate, polyetheretherketone (PEEK), polyamide, polyacetal, polythiophene, polyethyleneoxide, polytetrafluoroethylene, and PMMA; non-degradable polymers selected from the group comprising polyurethane, epoxy resin, and polysiloxane; and biodegradable polymers selected from the group comprising poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, polyglycolide-co-caprolactone, polydioxanone, polytrimethylene-carbonate, polyglycolide-co-dioxanone, polyamide ester, polypeptide, polyortho-esters, polymaleic acid, polyphosphazene, polyanhydride, polycebacicanhydride, polyhydroxyalkanoate, polyhydroxy butylate, polycyanoacrylate.

The biomedical implant may suppress interfacial delamination between the basic ceramic particles and the first and second biodegradable polymers and improve their mechanical property with the effect of suppressing inflammation.

The method to prepare a ceramic complex comprises following steps: (1) obtaining surface-modified basic ceramic particles by modifying the basic ceramic particles with first biodegradable polymers; and (2) mixing the surface-modified basic ceramic particles and second biodegradable polymers to be combined and to form stereo complex with the first biodegradable polymers included in the surface-modified basic ceramic particles.

Before the step (1), the method may further comprise a step (3) which is controlling a diameter of the basic ceramic particles.

The basic ceramic particles can adjust their surface area with changing their diameters, using mills such as bead mill, ball mill, and disk mill; homogenizer; mixer; crusher; pulverizer; stonebreaker; and ultrasonic application. The diameter can be in the range of 1 nm to 1 mm, whereby surface modification of the particles can be accomplished properly and reduction of physical property can be minimized by reducing crack development in the polymer matrix formed on the ceramic particle.

The basic ceramic particles may be purchased as finished products or may be manufactured from one selected from the group comprising lithium nitrate, beryllium nitrate, sodium nitrate, magnesium nitrate, potassium nitrate, calcium nitrate, rubidium nitrate, strontium nitrate, barium nitrate, cesium nitrate, francium nitrate, radium nitrated, and a combination thereof.

The first biodegradable polymer may include one selected from the group comprising poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D, L-lactide-co-caprolactone, polyglycolide-co-caprolactone, polydioxanone, polytrimethylene-carbonate, polyglycolide-co-dioxanone, polyamide ester, polypeptide, polyortho-esters, polymaleic acid, polyphosphazene, polyanhydride, polycebacicanhydride, polyhydroxyalkanoate, polyhydroxy butylate, polycyanoacrylate, and a combination thereof. Monomers for forming the first biodegradable polymers may be one selected from L-lactide, D-lactide, D,L-lactide, glycolide, caprolactone, dioxanone, trimethylene carbonate, hydroxy alkanoate, peptide, cyanoacrylate, lactic acid, glycolic acid, hydroxy caproic acid, maleic acid, phosphagen, amino acid, hydroxy butyric acid, sebacic acid, hydroxyethoxy acetic acid, trimethylene glycol, and a combination thereof.

The step (1) may include a step to obtain the basic ceramic particles whose surfaces are modified with the first biodegradable polymers by conducting a ring-opening polymerization or condensation polymerization with the monomers.

In case of modifying the surface of the basic ceramic particles with ring-opening polymerization, the surface modification process may be accomplished by including 1 wt % to 99 wt % of the basic ceramic particles and 1 wt % to 99 wt % of the monomers for forming the above first biodegradable polymers. In case of applying less than 1 wt % of the basic ceramic particles, the content of polymer against the surface area of ceramic particles may be so as large to make neutralization functions of the ceramic particles insignificant, and in case the content of the ceramic particles exceeds 99 wt %, the surface of the ceramic particles may not be modified sufficiently.

The ring-opening polymerization may be accomplished through vacuum heating using 0.001 wt % to 5.0 wt % of typical ring-opening catalyst with respect to total weight of the ceramic particles and the monomers which form the first biodegradable polymers, wherein the ring-opening catalyst may be at least one selected from the group comprising tin powder, stannous octoate, dibutyl tin dilaurate, dibutyltin dibromide, dibutyltin dichloride, tin(II) chloride, tin(IV) chloride, tin oxide, zinc powder, diethyl zinc, zinc octoate, zinc chloride, and dodecylbenzenesulfonic acid. The above ring-opening polymerization reaction may be performed at 50 to 300° C. of reaction temperature for 1 to 60 hours and in this case, an optimal polymerization condition for surface modification and polymerization of the ceramic particles can be prepared.

In case of modifying the surface of the basic ceramic particles with condensation polymerization, the surface modification process may be accomplished by including 1 wt % to 99 wt % of the basic ceramic particles and 1 wt % to 99 wt % of the monomers for forming the first biodegradable polymers. In case of applying less than 1 wt % of the basic ceramic particles, the content of polymer against the surface area of ceramic particles may be so as large to make neutralization functions of the ceramic particles insignificant and in case that the content of the ceramic particles exceeds 99 wt %, the surface of the ceramic particles may not be modified sufficiently. The condensation polymerization is conducted by vacuum heating. The condensation polymerization may be performed at 60 to 350° C. for 1 to 120 hours and in the above condition, the condensation polymerization of monomers can be progressed optimally.

The ceramic complex comprising a surface-modified basic ceramic particle and second biodegradable polymers can form a core-shell structure in which basic ceramic particle is a core and the first and second biodegradable is a shell.

The surface-modified ceramic particles can be obtained by dissolving the first biodegradable polymer in a solvent, scattering the basic ceramic particles at a rate of 10 to 100,000 rpm using ultra sonic waves and homogenizer, and then collecting the particles. The solvent may be one selected from the group consisting of chloroform, acetone, tetrahydrofuran, dioxane, acetonitrile, methylene chloride, toluene, xylene, benzene, hexafluoroisopropane, and a combination thereof.

Since the description on types and effects of the second biodegradable polymers which form the stereo complex with the first biodegradable polymers in the above second step is the same as was explained in the biomedical implant, it is therefore omitted herein.

The step (2) may be accomplished by including 1 to 99 wt % of the surface-modified basic ceramic particles and 1 to 99 wt % of the second biodegradable polymers to be combined with the first biodegradable polymers to form stereocomplex. When the content of the ceramic particles increases, the speed and an amount of the neutralization materials form the ceramic complex increases, and they can be controlled by adjusting the content of ceramic particles and the content of the first and second biodegradable polymers. In addition, the physical property of ceramic complex can be increased, using the stereo complex structure of the first biodegradable polymers located on the surface of the basic ceramic particles and the second biodegradable polymers.

Another method to prepare a biomedical implant comprises a process of preparing a biomedical implant including the ceramic complex.

The biomedical implant comprises a coating layer including the ceramic complex. The coating layer is prepared with a coating solution. The coating solution may include 1 wt % to 99 wt % of the surface-modified basic ceramic particles and 1 wt % to 99 wt % of the second degradable polymers. The first biodegradable polymer in the surface-modified basic ceramic particles and the second biodegradable polymers combine and subsequently form stereocomplex, by which the speed and the amount of materials supplied for neutralizing the byproduct from the polymers can be controlled with improving the mechanical strength.

Any known coating methods, such as ultrasonic method, spray method, dipping method, spin coating method, electrolytic coating method, and chemical/physical vapor deposition method may be used for forming the coating layer.

Such biomedical implant may prevent interfacial delamination between the basic ceramic particles and the polymers including the first and the second biodegradable polymers and improve their mechanical strength.

In order to evaluate the characteristics of the biomedical implants prepared according to examples of the present invention and comparative examples, their mechanical tensile strength were determined with Instron in accordance with the method of ASTM D638, and pH changes were observed 8 weeks after biodegradation. In addition, cell inflammations and cytotoxicity were evaluated with the degree of COX-2 expression, which is an enzyme responsible for inflammation, and cytotoxicity experiment, respectively.

Example 1

40 wt % of hydrated magnesium oxide and 60 wt % of D-lactide, their diameter having been adjusted to 1 μm through a homogenizer, and 0.15 wt % of stannous octoate as a catalyst, with respect to total weight of the reactants (hydrated magnesium oxide and D-lactide) was diluted in toluene and added into a glass reactor. Toluene and moisture were removed then completely, maintaining the glass reactor containing the above reactants under vacuum condition at 80° C. for 6 hours during agitating. Temperature of the sealed glass reactor was adjusted to 140° C., and the reactants were subjected to ring-opening polymerization for 30 hours, agitating the reactor in an oil bath. After completion of the polymerization, the polymers were collected and placed into chloroform, stirred for more than 1 hour, and then filtered out to obtain hydrated magnesium oxide particles of which surface was modified with poly-D-lactide by removing homo polymers and non-reacted materials.

Next, 30 wt % of the surface-modified hydrated magnesium oxide particles prepared by the above method and 70 wt % of poly-L-lactide biodegradable polymers were mixed to prepare completely biodegradable stents in which stereo complex was formed and their tensile strength, pH change, inflammation reaction, and cytotoxicity were observed and described in Table 1.

As shown in Table 1, the tensile strength of the stent prepared by Example 1 was improved remarkably, its pH was neutralized, the inflammation reaction was suppressed completely, and cytotoxicity did not appear.

Example 2

60 wt % of hydrated calcium oxide ceramic particles of which diameter was adjusted to 10 μm through a bead mill and 40 wt % of L-lactic acid were put into a glass reactor and maintained under vacuum at 70° C. for 6 hours during agitation, to remove moisture completely. Temperature of the glass reactor was adjusted to 140° C. and the reactants were subjected to condensing-polymerization for 30 hours in an oil bath. Non-reacted materials were removed from the recovered polymers with same method as described in Example 1, to obtain hydrated calcium oxide ceramic particles of which surface was modified with poly-L-lactide.

Next, 20 wt % of the surface-modified hydrated calcium oxide particles prepared by the above method and 80 wt % of poly-D-lactide biodegradable polymers were mixed to prepare a surgical suture in which stereo complex was formed and their tensile strength, pH change, inflammation reaction, and cytotoxicity were measured and described in Table 1. As shown in Table 1, the tensile strength was improved remarkably similar to the results of Example 1, its pH was neutralized, the inflammation reaction was suppressed completely, and cytotoxicity did not appear.

Example 3

10 wt % of D,L-lactide dissolved in 85 wt % of chloroform and adding 5 wt % of magnesium oxide ceramic particles of which diameter was not adjusted to the above mixture, ring-opening polymerization was conducted with same method described in Example 1 to prepare magnesium oxide ceramic particles of which surface was modified with poly-D,L-lactide.

15 wt % of the surface-modified hydrated magnesium oxide ceramic particles prepared by the above method and 85 wt % of poly-L-lactide biodegradable polymers were mixed to prepare a scaffold for tissue regeneration in which stereo complex was formed and their tensile strength, pH change, inflammation reaction, and cytotoxicity were measured and described in Table 1. As noted in Table 1, the tensile strength was remarkably improved, pH became neutral, the inflammation reaction was completely suppressed, and cytotoxicity did not appear. Although the tensile strength was improved remarkably, it was slightly lower than the results of Examples 1 and 2.

Comparative Example 1

Using 10 wt % of hydrated barium oxide ceramic particles of which diameter was adjusted to 5 μm through a pulverizer and 90 wt % of glycolide, ring-opening polymerization was conducted with same method described in Example 1 to prepare the hydrated barium oxide ceramic particles of which surface was modified with polyglycolide.

30 wt % of the surface-modified hydrated barium oxide ceramic particles prepared by the above method and 70 wt % of polydioxanone were mixed to prepare nano-fibers in which stereo complex was not formed and their tensile strength, pH change, inflammation reaction, and cytotoxicity were measured and described in Table 1. As noted in Table 1, the results of Comparative Example 1 were similar to the results of Example 1 in other physical properties, but the physical property was lower.

Comparative Example 2

Using 20 wt % of potassium oxide ceramic particles of which diameter was adjusted to 100 μm and 80 wt % of caprolactone, ring-opening polymerization was conducted with same method described in Example 1 to prepare the hydrated potassium oxide ceramic particles of which surface was modified with polycaprolactone.

95 wt % of the surface-modified potassium oxide ceramic particles prepared by the above method and 5 wt % of polyglycolide were mixed to prepare bio-sponge in which stereo complex was not formed and their tensile strength, pH change, inflammation reaction, and cytotoxicity were measured and described in Table 1. As noted in Table 1, the results of Comparative Example 2 were similar to the results of Example 1 in other physical properties, but the physical property was lower.

Comparative Example 3

Using 40 wt % of magnesium oxide ceramic particles of which diameter was adjusted to 500 μm through a mixer, 42 wt % of lactide and 18 wt % of caprolactone, ring-opening polymerization was conducted with same method described in Example 1 to prepare magnesium oxide ceramic particles of which surface was modified with polylactide-co-caprolactone.

35 wt % of the surface-modified magnesium oxide ceramic particles prepared by the above method and 65 wt % of polylactide-co-caprolactone were mixed to prepare hydrogel in which stereo complex was not formed and their tensile strength, pH change, inflammation reaction, and cytotoxicity were measured and described in Table 1. As noted in Table 1, the results of Comparative Example 3 were similar to the results of Example 1 in other physical properties, but the physical property was lower.

Comparative Example 4

Using 10 wt % of barium oxide ceramic particles of which diameter was adjusted to 20 μm through a crusher and 90 wt % of hydroxy caproic acid, ring-opening polymerization was conducted with same method described in Example 2 to prepare the barium oxide ceramic particles of which surface was modified with polycaprolactone.

10 wt % of the surface-modified barium oxide ceramic particles prepared by the above method and 90 wt % of polypeptide were mixed to prepare neurosurgery materials in which stereo complex was not formed and their tensile strength, pH change, inflammation reaction, and cytotoxicity were measured and described in Table 1. As noted in the results of Table 1, when comparing the results of Comparative Example 4 with those of Example 1, the physical property was somewhat lower and the inflammation reaction and the cytotoxicity were suppressed only to some extent.

Comparative Example 5

Hydrated magnesium oxide ceramic particles with polyglycolide-co-caprolactone surface modification were synthesized with magnesium nitrate and hydrated potassium oxide and using 50 wt % of the hydrated magnesium oxide ceramic particles of which diameter was not adjusted, 25 wt % of glycolic acid and 25 wt % of hydroxy caproic acid, condensation polymerization was conducted with same method described in Example 2.

5 wt % of the surface-modified hydrated magnesium oxide ceramic particles prepared by the above method and 95 wt % of polydioxanone were mixed to prepare orthopedic surgery materials in which stereo complex was not formed and their tensile strength, pH change, inflammation reaction, and cytotoxicity were measured and described in Table 1. As noted in Table 1, when comparing the results of Comparative Example 5 with those of Example 1, the physical property was somewhat lower and the inflammation reaction and the cytotoxicity were suppressed only to some extent.

Comparative Example 6

Hydrated magnesium oxide ceramic particles were synthesized with magnesium nitrate and hydrated calcium oxide and using 70 wt % of the hydrated magnesium oxide ceramic particles of which diameter was adjusted to 200 nm through a homogenizer, 30 wt % of polylactide, magnesium oxide ceramic particles of which surface was modified with polylactide according to the core-shell method described in Example 3.

70 wt % of the surface-modified magnesium oxide ceramic particles prepared by the above method and 30 wt % of polyhydroxyalkanoate were mixed to prepare plastic surgery materials in which stereo complex was not formed and their tensile strength, pH change, inflammation reaction, and cytotoxicity were measured and described in below Table 1. As noted in the Table 1, the results of Comparative Example 6 were similar to the results of Example 1 in other physical properties, but the physical property was lower.

Comparative Example 7

Hydrated calcium oxide ceramic particles were synthesized with calcium nitrate and hydrated sodium oxide and using 20 wt % of the hydrated sodium oxide ceramic particles of which diameter was adjusted to 400 nm through a crusher, 80 wt % of polymaleic acid, the cesium oxide ceramic particles of which surface was modified with polymaleic acid according to the core-shell method described in the above Example 3.

10 wt % of the surface-modified cesium oxide ceramic particles prepared by the above method and 90 wt % of polypeptide were mixed and coated to cobalt-chromium stent in which stereo complex was not formed and their tensile strength, pH change, inflammation reaction, and cytotoxicity were measured and described in Table 1. As noted in the results of Table 1, when comparing the results of Comparative Example 7 with those of Example 1, the physical property was somewhat lower, and the inflammation reaction and the cytotoxicity were suppressed only to some extent.

Comparative Example 8

Hydrated barium oxide ceramic particles were synthesized with barium nitrate and hydrated calcium oxide and using 70 wt % of the hydrated barium oxide ceramic particles of which diameter was adjusted to 1 μm through a bead mill, 30 wt % of lactide, ring-opening polymerization was conducted with same method described in Example 1 to prepare calcium oxide ceramic particles of which surface was modified with polylactide.

40 wt % of the surface-modified calcium oxide ceramic particles prepared by the above method and 60 wt % of polylactide were mixed and coated with titanium series dental implant in which stereo complex structure was not formed. Tensile strength, pH change, inflammation reaction, and cytotoxicity were measured and described in Table 1. As noted in the results of Table 1, when comparing the results of Comparative Example 8 with those of the Example 1, the physical property was somewhat lower and the inflammation reaction and the cytotoxicity were suppressed only to some extent.

Comparative Example 9

Hydrated potassium oxide ceramic particles were synthesized with potassium nitrate and hydrated sodium oxide and using 40 wt % of the hydrated potassium oxide ceramic particles of which diameter was not adjusted and 60 wt % of trimethylene carbonate, ring-opening polymerization was conducted with same method described in Example 1 to prepare hydrated potassium ceramic particles.

20 wt % of the surface-modified potassium oxide ceramic particles prepared by the above method and 80 wt % of polyglycolide were mixed and coated with hydroxyapatite orthopedic surgery materials in which stereo complex structure was not formed. Tensile strength, pH change, inflammation reaction, and cytotoxicity were measured and described in Table 1. As noted in Table 1, the results of Comparative Example 8 were similar to the results of Example 1 in other physical properties, but the physical property was lower.

Comparative Example 10

Using 80 wt % of magnesium oxide ceramic particles of which diameter was adjusted to 400 nm through ultra sonic treatment and 20 wt % of hydroxy caproic acid, condensation polymerization was conducted with same method described in Example 2 to prepare the magnesium oxide ceramic particles of which surface was modified with polycaprolactone.

50 wt % of the surface-modified magnesium oxide ceramic particles prepared by the above method and 50 wt % of polylactide-co-glycolide were mixed and coated the surface of non-degradable polyurethane stent in which stereo complex structure was not formed. Tensile strength, pH change, inflammation reaction, and cytotoxicity were measured and described in Table 1. As noted in Table 1, the results of Comparative Example 10 were similar to the results of Example 1 in other physical properties, but the physical property was lower.

Comparative Example 11

A test sample was prepared using polylactide biodegradable polymers which did not contain ceramic particles. Tensile strength, pH change, inflammation reaction, and cytotoxicity were measured and described in Table 1. As noted in Table 1, the results of Comparative Example 11 show that the tensile strength was very low, pH maintained acidity, the inflammation reaction was very severe, and the cytotoxicity was also remarkable.

Comparative Example 12

5 wt % of hydrated magnesium oxide ceramic particles of which surface and diameter were not adjusted and 95 wt % of polylactide biodegradable polymers were mixed to prepare a test sample and their tensile strength, pH change, inflammation reaction, and cytotoxicity were measured and described in Table 1. As noted in Table 1, the results of Comparative Example 12 show that the tensile strength was very low, pH was weak acidic, the inflammation reaction and the cytotoxicity were suppressed only to some extent.

TABLE 1

Comparison of characteristics containing ceramic particles

| Classification | Neutralizing ceramic particles | Tensile strength (MPa) | pH (8 weeks) | Inflammation reaction | Cytotoxicity |
|---|---|---|---|---|---|
| Example 1 | Surface-modified | 71 | 7.2 | Completely suppressed | X |
| Example 2 | Surface-modified | 73 | 7.3 | Completely suppressed | X |
| Example 3 | Surface-modified | 68 | 7.1 | Completely suppressed | X |
| Comparative Example 1 | Surface-modified | 57 | 6.9 | Completely suppressed | X |
| Comparative Example 2 | Surface-modified | 55 | 7.4 | Completely suppressed | X |
| Comparative Example 3 | Surface-modified | 54 | 7.1 | Completely suppressed | X |
| Comparative Example 4 | Surface-modified | 59 | 6.4 | Partially suppressed | Δ |
| Comparative Example 5 | Surface-modified | 58 | 6.1 | Partially suppressed | Δ |
| Comparative Example 6 | Surface-modified | 57 | 7.3 | Completely suppressed | X |
| Comparative Example 7 | Surface-modified | 53 | 6.3 | Partially suppressed | Δ |
| Comparative Example 8 | Surface-modified | 57 | 6.4 | Partially suppressed | Δ |
| Comparative Example 9 | Surface-modified | 55 | 6.9 | Completely suppressed | X |
| Comparative Example 10 | Surface-modified | 53 | 6.7 | Completely suppressed | X |
| Comparative | Not | 35 | 4.0 | Very severe | ○ |

TABLE 1-continued

Comparison of characteristics containing ceramic particles

| Classification | Neutralizing ceramic particles | Tensile strength (MPa) | pH (8 weeks) | Inflammation reaction | Cytotoxicity |
|---|---|---|---|---|---|
| Example 11 Comparative Example 12 | contained Surface unmodified | 26 | 5.8 | Partially suppressed | Δ |

Under the cytotoxicity column in Table 1, X indicated a case where less than 10% of cells had died, Δ indicated a case where 10% to 30% of cell death had appeared and ○ indicated a case where over 30% of cell death had appeared.

The foregoing embodiments and advantages are merely exemplary and are not to be construed as limiting the present disclosure. The present teachings can be readily applied to other types of apparatuses. This description is intended to be illustrative, and not meant to limit the scope of the claims.

Many alternatives, modifications, and variations will be apparent to those skilled in the art. The features, structures, methods, and other characteristics of the exemplary embodiments described herein may be combined in various ways to obtain additional and/or alternative exemplary embodiments. As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or their equivalents and bounds are therefore intended to be embraced by the appended claims.

What is claimed is:

1. A biomedical implant comprising a ceramic complex, wherein the ceramic complex comprises:
   surface-modified basic ceramic particles, which are basic ceramic particles with their surface modified with first biodegradable polymers; and
   second biodegradable polymers, which are combined with the first biodegradable polymers to form a stereo complex;
   wherein the content of the first biodegradable polymers and the second biodegradable polymers is 5 to 95 wt % and the content of basic ceramic particles is 5 to 95 wt % with respect to the total weight of the ceramic complex,
   wherein the surface-modified basic ceramic particles form a core-shell structure in which the basic ceramic particles are a core and the first biodegradable polymers are a shell, and
   wherein the surface-modified basic ceramic particles are in the matrix of the stereo complex.

2. The biomedical implant according to claim 1, wherein the surface-modified basic ceramic particles are capable of neutralizing acidic byproducts generated from degradation of a polymer having biocompatibility.

3. The biomedical implant according to claim 1, wherein the surface-modified basic ceramic particles are included in a coating layer formed on the surface of the biomedical implant.

4. The biomedical implant according to claim 1, wherein the diameter of the surface-modified basic ceramic particles is in range of 1 nm to 1 mm.

5. The biomedical implant according to claim 1, wherein the first and the second biodegradable polymer are different and are selected from the group consisting of poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, polyglycolide-co-caprolactone, polydioxanone, polytrimethylene-carbonate, polyglycolide-co-dioxanone, polyamide ester, polypeptide, polyortho-ester, polymaleic acid, polyphosphazene, polyanhydride, polycebacicanhydride, polyhydroxyalkanoate, polyhydroxy butylate, polycyanoacrylate, and a combination thereof.

6. The biomedical implant according to claim 1, wherein the biomedical implant is selected from the group consisting of cardiovascular system materials comprising of surgical suture, scaffold for tissue regeneration and bio-nano fiber; dental materials consisting of a pin, screw and bar; surgical materials; fillers for plastic surgery; and bio-materials consisting of a bio-sensor and drug delivery system reservoir.

* * * * *